United States Patent [19]

Fuchs et al.

[11] Patent Number: 4,485,252
[45] Date of Patent: Nov. 27, 1984

[54] 2-PHENYL-ALK-1-ENYL-CYCLOPROPANE-CARBOXYLIC ACID INTERMEDIATES

[75] Inventors: Rainer Fuchs, Wuppertal; Ingeborg Hammann, Cologne; Bernhard Homeyer, Leverkusen; Wilhelm Stendel, Wuppertal, all of Fed. Rep. of Germany

[73] Assignee: Bayer Aktiengesellschaft, Leverkusen, Fed. Rep. of Germany

[21] Appl. No.: 375,061

[22] Filed: May 5, 1982

Related U.S. Application Data

[62] Division of Ser. No. 143,958, Apr. 25, 1980, Pat. No. 4,344,963.

[30] Foreign Application Priority Data

May 23, 1979 [DE] Fed. Rep. of Germany ....... 2920947

[51] Int. Cl.³ .................... C07C 69/743; C07C 61/04
[52] U.S. Cl. ........................................ 560/8; 562/405; 260/544 D
[58] Field of Search ........................... 560/8; 562/405; 260/544 D

[56] References Cited

U.S. PATENT DOCUMENTS 4,157,447  6/1979  Engel ...................................... 560/8

*Primary Examiner*—Dolph H. Torrence
*Attorney, Agent, or Firm*—Sprung Horn Kramer & Woods

[57] ABSTRACT

2-Phenyl-alk-1-enyl-cyclopropane-carboxylic acid esters of the formula

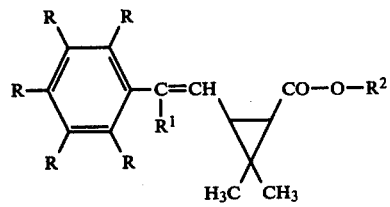

in which
R each independently is hydrogen, halogen, cyano, nitro and, in each case optionally halogen-substituted, alkyl, alkoxy, alkylenedioxy or alkylthio,
$R^1$ is optionally halogen-substituted alkyk, and
$R^2$ is a radical customary in the alcohol part of pyrethroids which exhibit insecticidal and acaricidal activity. They are made from the corresponding alkyl esters which are new and made by novel processes.

2 Claims, No Drawings

2-PHENYL-ALK-1-ENYL-CYCLOPROPANE-CARBOXYLIC ACID INTERMEDIATES

This is a division of application Ser. No. 143,958, filed Apr. 25, 1980 now U.S. Pat. No. 4,344,963.

The invention relates to certain new 2-phenyl-alk-1-enyl-cyclopropane-carboxylic acid esters, to a process for their preparation, and to their use as arthropodicides, especially as insecticides and acaricides. It also relates to intermediate products for the preparation of said esters.

It is known that certain 2-phenyl-alk-1-enyl-cyclopropane-carboxylic acid esters, for example 3-(2-phenylvinyl)-2,2-dimethyl-cyclopropane-1-carboxyic acid 3-phenoxy-benzyl ester and 3-(2-(4-chloro-phenyl)-vinyl)-2,2-dimethyl-cyclopropane-1-carboxylic acid 3-phenoxy-α-cyanobenzyl ester, are insecticidally and acaricidally active (see DE-OS's (German Published Specifications) 2,706,184, 2,738,150 and 2,730,515).

However, the action of these compounds is not always satisfactory, especially in the case of low concentrations of active compound and when small amounts are applied.

The present invention now provides:

(1), as new compounds, the 2-phenyl-alk-1-enyl-cyclopropanecarboxylic acid esters of the general formula

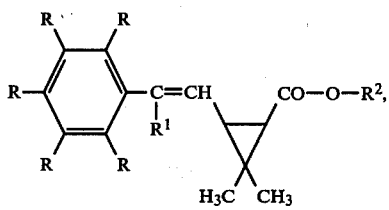

in which
R independently represents hydrogen, halogen, cyano, nitro and, in each case optionally halogen-substituted, alkyl, alkoxy, alkylenedioxy and alkylthio,
$R^1$ represents optionally halogen-substituted alkyl and
$R^2$ represents a radical customary in the alcohol part of pyrethroids;

(2) a process for the preparation of a 2-phenyl-alk-1-enyl-cyclopropane-carboxylic acid ester of the general formula(I), characterized in that a 2-phenyl-alk-1-enyl-cyclopropane-carboxylic acid of the general formula

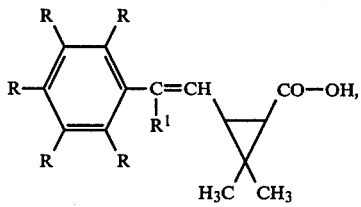

in which
R and $R^1$ have the meanings indicated above,
or a reactive derivative thereof, is reacted with an alcohol of the general formula

HO—$R^2$  (III), in which
$R^2$ has the meaning indicated above,
or with a reactive derivative thereof, if appropriate in the presence of an acid acceptor and if appropriate using a diluent;

(3), as new compounds, the 2-phenyl-alk-1-enyl-cyclopropanecarboxylic acids of the general formula

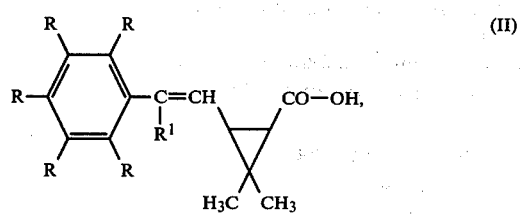

in which
R and $R^1$ have the meanings indicated under (1);

(4) a process for the preparation of a 2-phenyl-alk-1-enyl-cyclopropanecarboxylic acid of the formula (II), which is characterized in that an alkyl ester of the general formula

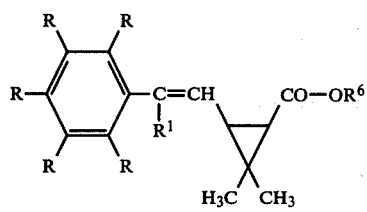

in which
R and $R^1$ have the meanings indicated under (1) and
$R^6$ represents $C_1$–$C_4$-alkyl,
is saponified;

(5), as new compounds, the 2-phenyl-alk-1-enyl-cyclopropanecarboxylic acid alkyl esters of the general formula

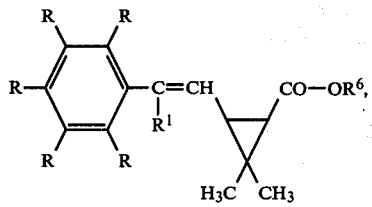

in which
R and $R^1$ have the meanings indicated under (1) and
$R^6$ represents $C_1$–$C_4$-alkyl;

(6) a process for the preparation of a 2-phenyl-alk-1-enyl-cyclopropane-carboxylic acid alkyl ester of the formula (IIb), characterized in that (a) a 1-phenyl-alkane-phosphonic acid ester of the general formula (V)

in which
R and R¹ have the meanings indicated under (1) and
R⁷ represents $C_1$–$C_4$-alkyl, phenyl or $C_2$–$C_5$-alkanediyl,
is reacted with a 2,2-dimethyl-3-formyl-cyclopropane-1-carboxylic acid alkyl ester of the general formula (VI)

in which
R⁶ represents $C_1$–$C_4$-alkyl,
in the presence of a base and if appropriate in the presence of a diluent, at a temperature between 0° and 100° C.,
or (b) a diene of the general formula (VII)

in which
R and R¹ have the meanings indicated under (1),
is reacted with a diazoacetic acid ester of the general formula $$N_2CH—CO—OR^6 \quad (VIII),$$

in which
R⁶ represents $C_1$–$C_4$-alkyl,
in the presence of a catalyst, at a temperature between 50° and 200° C.;

(7) as new compounds, 1-phenyl-alkanephosphonic acid esters of the general formula (V)

in which
R and R¹ have the meanings indicated under (1) and
R⁷ represents $C_1$–$C_4$-alkyl, phenyl or $C_2$–$C_5$-alkanediyl;

(8) a process for the preparation of a 1-phenyl-alkanephosphonic acid ester of the general formula (V), which is characterized in that a phosphorous acid ester of the general formula $$R^8—\overset{O}{\overset{\|}{P}}(OR^7)_2, \quad (IX)$$

in which
R⁷ has the meaning indicated above and
R⁸ represents hydrogen or $C_1$–$C_4$-alkyl,
is reacted with a halogeno-1-phenyl-alkane of the general formula (X)

in which
R and R¹ have the meanings indicated under (1) and
X represents chlorine, bromine or iodine,
if appropriate in the presence of a base and if appropriate using a diluent, between 20° and 150° C.;

(9), as new compounds, the dienes of the general formula (VII)

in which
R and R¹ have the meanings indicated under (1);
and

(10) a process for the preparation of a diene of the formula (VII), which is characterized in that an alkyl phenyl ketone of the general formula (XI)

in which
R and R¹ have the meanings indicated under (1),
is reacted with 3-methyl-but-2-enyl-triphenyl-phosphonium bromide, of the formula (XII)

in the presence of a strong base and if appropriate using a diluent, at a temperature between −70° and +100° C.

The 2-phenyl-alk-1-enyl-cyclopropane-carboxylic acid esters of the formula (I) are distinguished by a high insecticidal and acaricidal activity.

Surprisingly, the 2-phenyl-alk-1-enyl-cyclopropanecarboxylic acid esters according to the invention exhibit a considerably more powerful insecticidal and acaricidal action than compounds, known from the state of the art, of analogous structure and the same type of action.

Preferred compounds of the formula (I) are those in which

R represents hydrogen, one or two radicals selected from the group consisting of fluorine, chlorine, bromine, $C_1$-$C_4$-alkyl, $C_1$-$C_2$-fluoroalkyl, $C_1$-$C_2$-chloroalkyl, $C_1$-$C_2$-chlorofluoroalkyl, $C_1$-$C_4$-alkoxy, $C_1$-$C_4$-alkylthio, $C_1$-$C_2$-fluoroalkoxy and $C_1$-$C_2$-chlorofluoroalkoxy, $C_1$-$C_2$-alkylenedioxy or $C_1$-$C_2$-fluoroalkylenedioxy, $R^1$ represents $C_1$-$C_4$-alkyl, $C_1$-$C_2$-fluoroalkyl or $C_1$-$C_2$-chlorofluoro-alkyl and $R^2$ represents one of the radicals below (which are customary in the alcohol component of pyrethroids):

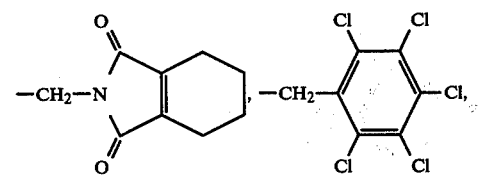

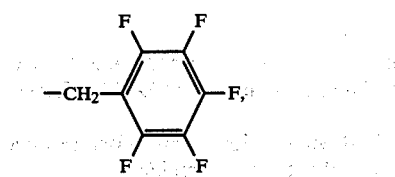

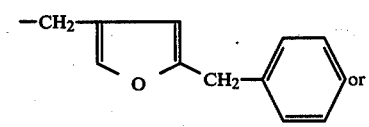

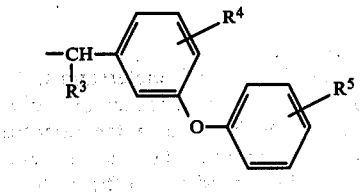

wherein $R^3$ represents hydrogen, cyano, ethynyl, methyl or ethyl and $R^4$ and $R^5$, which can be identical or different, represent hydrogen, fluorine, chlorine or bromine. The general formula (I) also includes the various possible stereoisomers and optically active isomers, and mixtures thereof.

In a preferred variant (a) of process (2) for the preparation of a compound of the formula (I), as a reactive derivative of a carboxylic acid of the formula (II), the corresponding carboxylic acid chloride of the general formula

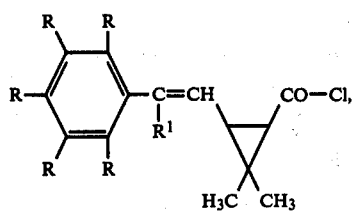

in which

R and $R^1$ have the meanings indicated under (1), is reacted with an alcohol of the formula (III), in the presence of an acid acceptor and using a diluent.

A particularly preferred variant (b) of process (2) for the preparation of a compound of the formula (I) in which $R^2$ represents optionally halogen-substituted 3-phenoxy-α-cyano-benzyl is characterized in that a carboxylic acid chloride of the formula (IIa) is reacted with an optionally halogen-substituted 3-phenoxy-benzaldehyde of the general formula

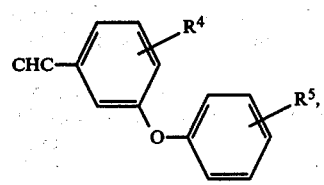

in which $R^4$ and $R^5$ have the meanings indicated above, and at least an equimolar amount of alkali metal cyanide (preferably sodium cyanide or potassium cyanide), if appropriate in the presence of a catalyst and using a diluent.

If B 3-(2-(4-fluoro-phenyl)-3,3,3-trifluoro-prop-1-enyl)-2,2-dimethyl-cyclopropane-1-carboxylic acid chloride and 3-phenoxy-benzyl alcohol, for example, are used as starting substances in process variant (a) and 3-(2-(4-methoxyphenyl)-pent-1-enyl)-2,2-dimethyl-cyclopropane-1-carboxylic acid chloride, sodium cyanide and 4-fluoro-3-phenoxybenzaldehyde are used as starting substances in variant (b), the corresponding reactions can be outlined by the following equations:

(a)

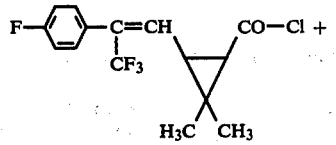

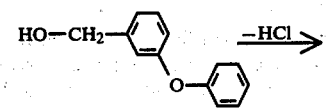

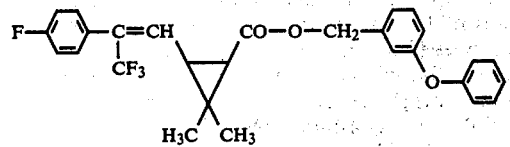

-continued

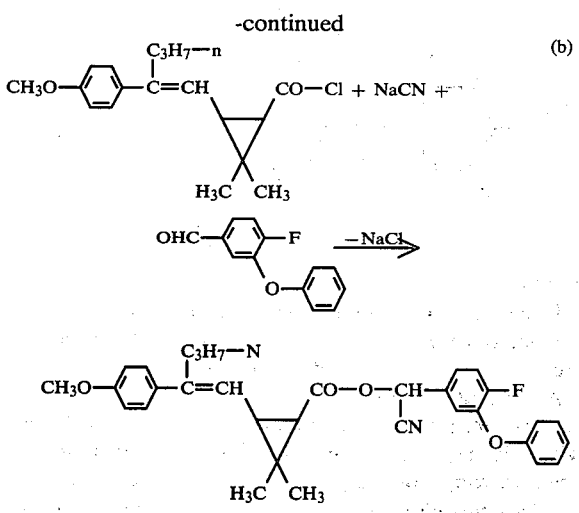

The formulae (II), (IIa), (III) and (IV) provide definitions of the starting substances for the preparation of the compounds of the formula (I). Preferably, in these formulae for the starting substances, R to $R^5$ have those meanings which have been mentioned as preferred for R to $R^5$ in formula (I).

The 2-phenyl-alk-1-enyl-cyclopropane-carboxylic acids (II), and the corresponding acid chlorides (IIa) as reactive derivatives thereof, to be used as starting compounds have not hitherto been disclosed in the literature.

Carboxylic acid chlorides of the formula (IIa) can be prepared from the corresponding carboxylic acids of the formula (II) by customary methods, for example by reaction with a chlorinating agent, for example thionyl chloride, if appropriate using a diluent, for example carbon tetrachloride, at a temperature between 10° and 100° C.

Carboxylic acids of the formula (II) are obtained from the corresponding alkyl esters of the formula

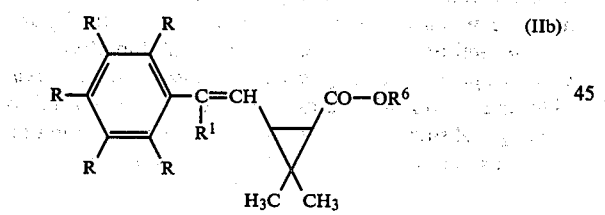

in which
R and $R^1$ have the meanings indicated under (1) and $R^6$ represents $C_1$–$C_4$-alkyl,
by customary saponification methods, for example by heating to temperatures between 50° and 150° C. with aqueous alcoholic sodium hydroxide solution for several hours. Working up is effected by customary methods, for example by distilling off the alcohol, diluting the residue with water, acidifying the mixture and extracting it with methylene chloride, drying the organic extracts and distilling off the solvent.

Examples which may be mentioned of the carboxylic acids of the formula (II) and the corresponding acid chlorides (IIa) and esters (IIb) are: 3-(2-phenyl-prop-1-enyl)-, 3-(2-phenyl-but-1-enyl)-, 3-(2-phenyl-3,3,3-trifluoro-prop-1-enyl)-, 3-(2-(4-fluoro-phenyl)-prop-1-enyl)-, 3-(2-(4-fluoro-phenyl)-but-1-enyl)-, 3-(2-(4-fluoro-phenyl)-3,3,3-trifluoro-prop-1-enyl)-, 3-(2-(3-chloro-phenyl)-prop-1-enyl)-, 3-(2-(4-chloro-phenyl)-prop-1-enyl)-, 3-(2-(4-chloro-phenyl)-but-1-enyl)-, 3-(2-(4-chloro-phenyl)-3,3,3-trifluoro-prop-1-enyl)-, 3-(2-(3-methyl-phenyl)-prop-1-enyl)-, 3-(2-(4-methylphenyl)-prop-1-enyl)-, 3-(2-(4-methyl-phenyl)-but-1-enyl)-, 3-(2-(4-methyl-phenyl)-3,3,3-trifluoro-prop-1-enyl)-, 3-(2-(4-methoxy-phenyl)-prop-1-enyl)-, 3-(2-(4-methoxy-phenyl)but-1-enyl)-, 3-(2-(4-methoxy-phenyl)-3,3,3-trifluoro-prop-1-enyl)-, 3-(2-(3,4-methylenedioxy-phenyl)-prop-1-enyl)-, 3-(2-(3,4-methylenedioxy-phenyl)-but-1-enyl)- and 3-(2-(3,4-methylenedioxy-phenyl)-3,3,3-trifluoro-prop-1-enyl-2,2-dimethyl-cyclopropane-1-carboxylic acid and the corresponding acid chlorides, the methyl esters and the ethyl esters.

2-Phenyl-alk-1-enyl-cyclopropanecarboxylic acid alkyl esters of the formula (IIb), and the corresponding acids (II) and acid chlorides (IIa) have not hitherto been described in the literature.

2-Phenyl-alk-1-enyl-cyclopropane-carboxylic acid esters of the formula (IIb) are obtained
(a) by reacting 1-phenyl-alkane-phosphonic acid esters of the general formula

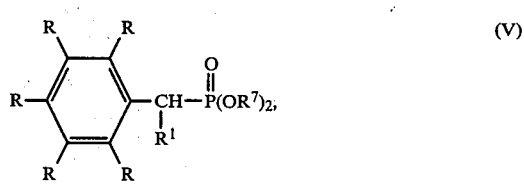

in which
R and $R^1$ have the meanings indicated under (1) and $R^7$ represents $C_1$–$C_4$-alkyl, phenyl or $C_2$–$C_5$-alkanediyl,
with 2,2-dimethyl-3-formyl-cyclopropane-1-carboxylic acid alkyl esters of the general formula

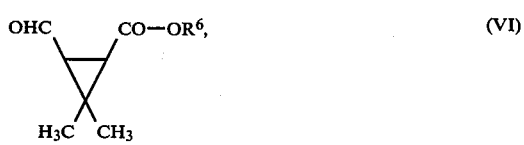

in which
$R^6$ represents $C_1$–$C_4$-alkyl,
in the presence of a base, for example potassium tert.-butylate, and if appropriate in the presence of a diluent, for example tetrahydrofuran, at a temperature between 0° and 100° C., preferably between 10° and 80° C. Working up can be carried out in the customary manner, for example by diluting the mixture with water and extracting it with methylene chloride, drying the organic phase, stripping off the solvent and purifying by vacuum distillation the product which remains.

Esters of the formula (IIb) are also obtained
(b) by reacting dienes of the general formula

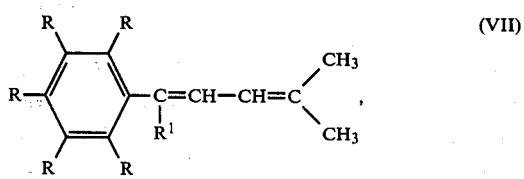

in which

R and $R^1$ have the meanings indicated under (1), with diazoacetic acid esters of the general formula $$N_2CH-CO-OR^6 \quad (VIII)$$

in which $R^6$ represents $C_1-C_4$-alkyl, in the presence of a catalyst, for example copper powder and copper sulphate, at a temperature between 50° and 200° C., preferably between 80° and 150° C.

For working up, the mixture is diluted with methylene chloride and filtered. The solvent is stripped off from the filtrate, after washing with water and drying, and the crude product which remains is optionally purified by vacuum distillation.

Formula (V) provides a definition of the 1-phenylalkane-phosphonic acid esters to be used as intermediate products. Preferably, in this formula, R and $R^1$ have those meanings which have been mentioned as preferred for R and $R^1$ in formula (I), and $R^7$ represents methyl, ethyl or phenyl or the two radicals $R^7$ together represent 2,2-dimethyl-propane-1,3-diyl.

Examples which may be mentioned are: 1-phenyl-, 1-(4-fluoro-phenyl)-, 1-(3-chloro-phenyl)-, 1-(4-chloro-phenyl)-, 1-(3-methyl-phenyl)-, 1-(4-methyl-phenyl)-, 1-(4-methoxy-phenyl)- and 1-(3,4-methylenedioxy-phenyl)-ethane-phosphonic acid dimethyl ester and diethyl ester; and 1-phenyl-, 1-(4-fluoro-phenyl)-, 1-(3-chloro-phenyl)-, 1-(4-chloro-phenyl)-, 1-(3-methyl-phenyl)-, 1-(4-methyl-phenyl)-, 1-(4-methoxy-phenyl)- and 1-(3,4-methylene-dioxy-phenyl)-propane-phosphonic acid dimethyl ester and diethyl ester.

The new 1-phenyl-alkane-phosphonic acid esters of the formula (V) are obtained by processes which are in themselves known, for example by reacting phosphorous acid esters of the general formula

$$R^8-P(OR^7)_2, \quad (IX)$$

in which $R^7$ has the meaning indicated above and $R^8$ represents hydrogen or $C_1-C_4$-alkyl, with 1-halogeno-1-phenyl-alkanes of the general formula

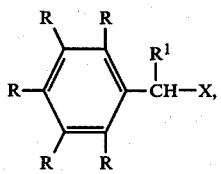

in which

R and $R^1$ have the meanings indicated under (1) and

X represents chlorine, bromine or iodine, if appropriate in the presence of a base, for example sodium methylate, and if appropriate using a diluent, for example methanol, at a temperature between 20° and 150° C.

Starting compounds of the formulae (IX) and (X) are known.

The 2,2-dimethyl-3-formyl-cyclopropane-1-carboxylic acid esters of the formula (VI) also to be used as intermediate products are known (see DE-OS (German Published Specification) 2,615,160). Examples which may be mentioned are 2,2-dimethyl-3-formyl-cyclopropane-1-carboxylic acid methyl ester and ethyl ester.

Formula (VII) provides a definition of the dienes also to be used as intermediate products. Preferably, in this formula, R and $R^1$ have those meanings which have been mentioned as preferred for R and $R^1$ in formula (I).

Examples which may be mentioned are: 2-phenyl-, 2-(4-fluoro-phenyl)-, 2-(3-chloro-phenyl)-, 2-(4-chloro-phenyl)-, 2-(3-methyl-phenyl)-, 2-(4-methyl-phenyl)-, 2-(4-methoxy-phenyl)- and 2-(3,4-methylenedioxy-phenyl)-1,1,1-trifluoro-5-methyl-hexa-2,4-diene.

The new dienes of the formula (VII) are obtained by processes which are in themselves known, for example by reacting alkyl phenyl ketones of the general formula

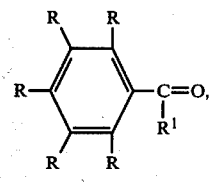

in which

R and $R^1$ have the meanings indicated under (1), with 3-methyl-but-2-enyl-triphenyl-phosphonium bromide, of the general formula

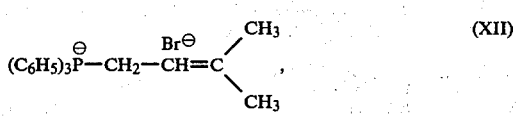

in the presence of a strong base, for example butyllithium, and if appropriate using a diluent, for example tetrahydrofuran or hexane, at a temperature between −70° and +100° C., preferably between −20° and +50° C. For working up, the mixture is diluted with water and extracted several times with a water-immiscible solvent, for example petroleum ether. After drying, the solvent is stripped off from the combined extracts and the crude product which remains in the residue is optionally purified by vacuum distillation.

Starting compounds of the formulae (XI) and (XII) are known.

Alcohols of the formula (III), and aldehydes of the formula (IV) as compounds to be derived therefrom, which are used as reactants in the process indicated above under (2), for the preparation of the new 2-phenyl-alk-1-enyl-cyclopropane-carboxylic acid esters of the formula (I), are known (see DE-OS's (German Published Specifications) Nos. 2,005,489, 2,326,077 and 2,709,264; and British Patent Specification No. 1,078,511).

Preferably, $R^2$ and/or $R^3$, $R^4$ and $R^5$ in the starting compounds of the formula (III) and of the formula (IV) have the meanings indicated as preferred for $R^2$, $R^3$, $R^4$ and $R^5$ in connection with the compounds of the formula (I).

Examples which may be mentioned are: tetrahydrophthalimidomethyl alcohol, pentafluorobenzyl alcohol, pentachlorobenzyl alcohol, 5-benzyl-3-furyl alcohol, 3-phenoxy-benzyl alcohol, 3-phenoxy-benzaldehyde, 3-(3-fluoro-phenoxy)-, 3-(4-fluoro-phenoxy)-, 3-phenoxy-4-fluoro-, 3-(3-fluoro-phenoxy)-4-fluoro- and 3-(4-fluorophenoxy)-4-fluoro-benzyl alcohol, 3-(3- fluoro-phenoxy)-, 3-(4-fluoro-phenoxy)-, 3-phenoxy-4-fluoro-, 3-(3-fluoro-phenoxy)-4-fluoro- and 3-(4-fluoro-phenoxy)-4-fluoro-α-cyano-benzyl alcohol, 3-(3-fluoro-phenoxy-), 3-(4-fluoro-phenoxy)-, 3-phenoxy-4-fluoro-, 3-(3-fluoro-phenoxy)-4-fluoro- and 3-(4-fluoro-phenoxy)-4-fluoro-α-ethynylbenzyl alcohol, 3-phenoxy-4-fluoro-α-methyl-benzyl alcohol and 3-(3-fluoro-phenoxy)-, 3-(4-fluoro-phenoxy)-, 3-phenoxy-4-fluoro-, 3-(3-fluoro-phenoxy)-4-fluoro- and 3-(4-fluoro-phenoxy)-4-fluoro-benzaldehyde.

All variants of the process indicated under (2) for the preparation of the 2-phenyl-alk-1-enyl-cyclopropanecarboxylic acid esters of the formula (I) are preferably carried out using a suitable solvent or diluent. Possible solvents and diluents are virtually any of the inert organic solvents. These include, as preferences, aliphatic and aromatic, optionally chlorinated hydrocarbons, such as pentane, hexane, heptane, benzene, toluene, xylene, methylene chloride, chloroform, carbon tetrachloride, chlorobenzene and o-dichlorobenzene; ethers, such as diethyl ether, dibutyl ether, tetrahydrofuran and dioxane; ketones, such as acetone, methyl ethyl ketone, methyl isopropyl ketone and methyl isobutyl ketone; and nitriles, such as acetonitrile and propionitrile.

When the reaction is carried out in a two-phase medium, water is used as the second solvent component.

Any of the customary acid-binding agents can be used as acid acceptors in variant (a) of the preparative process described under (2). Acid-binding agents which have proved particularly suitable are alkali metal carbonates and alcoholates, such as sodium carbonate and potassium carbonate and sodium methylate or ethylate and potassium methylate or ethylate, and furthermore aliphatic, aromatic or heterocyclic amines, for example triethylamine, trimethylamine, dimethylaniline, dimethylbenzylamine and pyridine.

Compounds which are usually used as auxiliaries for the phase transfer of reactants in reactions in multiphase media are, in general, used as catalysts in variant (b) of process (2). Tetraalkyl- and trialkylaralkyl-ammonium salts, for example tetrabutylammonium bromide and trimethyl-benzylammonium chloride, may be mentioned in particular.

The reaction temperature can be varied within a substantial range. In general, the reaction is carried out between 0° and 100° C., preferably between 10° and 50° C. in process variant (a) and preferably between 10° and 30° C. in variant (b).

In general, all the variants of the process according to the invention are carried out under normal pressure.

The starting substances are usually employed in equimolar amounts for carrying out process (2) according to the invention. An excess of one or the other of the reactants brings to substantial advantages. The reaction is in general carried out in one or more diluents in the presence of an acid acceptor or a catalyst, and the reaction mixture is stirred at the required temperature for several hours. The reaction mixture is then shaken with toluene/water and the organic phase is separated off, washed with water and dried.

After distilling off the solvent in vacuo, the new compounds are in general obtained in the form of oils, some of which cannot be distilled without decomposition, but which are freed from the last volatile constituents by so-called "incipient distillation", that is to say by prolonged heating to moderately elevated temperatures under reduced pressure, and are purified in this manner. The refractive index is used for their characterization.

As already mentioned, the 2-phenyl-alk-1-enyl-cyclopropane-carboxylic acid esters (I) are distinguished by a high insecticidal and acaricidal activity. They can be employed against insects and mites which are harmful to plants, in agriculture and forestry and in the protection of stored products and the hygiene field, and against ectoparasites in the field of veterinary medicine.

The active compounds are well tolerated by plants, have a favorable level of toxicity to warm-blooded animals, and can be used for combating arthropod pests, especially insects and acarids, which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example, *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni,* Car-

*pocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Cryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor, Agriotes spp., Conoderus spp., Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus Koleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

A liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.0001 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

The active compounds according to the invention are also suitable for combating ectoparasites and endoparasites in the field of veterinary medicine.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

The present invention also provides an anthropodicidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects or acarids) which comprises applying to the arthropods, or to a habitat thereof, a compound of the present invention alone or in the form of a composition containing as active ingredient a compound of the present invention in admixture with a diluent or carrier.

The present invention also provides a method of freeing or protecting domesticated animals from parasitical insects or acarids which comprises applying to said animals a compound according to the present invention, in admixture with a diluent or carrier.

The present invention further provides crops protected from damage by arthropods by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from parasitical insects or acarids by the application to said animals of a compound according to the present invention, in admixture with a diluent or carrier.

Preparation of the novel compounds is shown in the following illustrative examples:

EXAMPLE 1

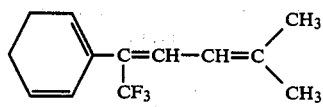

65 ml of 15% strength solution of n-butyl-lithium in hexane were added dropwise to a suspension of 41.1 g (0.1 mol) of dry 3,3-dimethylallyl-triphenyl-phosphonium bromide in 300 ml of anhydrous tetrahydrofuran at 0° C. under nitrogen, while stirring. The deep red solution thus obtained was stirred at 0° C. for a further 15 minutes and 17.4 g (0.1 mol) of ω, ω,ω-trifluoroacetophenone were then added dropwise at 0°-10° C. The mixture was subsequently stirred at room temperature until it was decolorized (about 12 hours). 600 ml of water were then added and the reaction mixture was extracted 5 times with 200 ml of petroleum ether each time. The petroleum ether phases were dried over magnesium sulphate and the solvent was then stripped off in a rotary evaporator under a waterpump vacuum. 150 ml of n-hexane were added to the residue and residual triphenyl-phosphine oxide was filtered off. The solvent was subsequently distilled off from the filtrate under normal pressure and the oily residue was then distilled in vacuo, 12.8 g (56.6% of theory) of 1,1,1-trifluoro-2-phenyl-5-methyl-hexa-2,4-diene were obtained as a slightly reddish liquid with a boiling point of 80°-85° C. under 3 mbar.

The following compounds were obtained analogously:

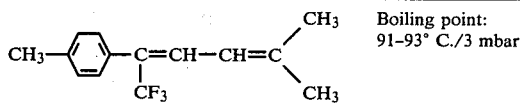 Boiling point: 91-93° C./3 mbar

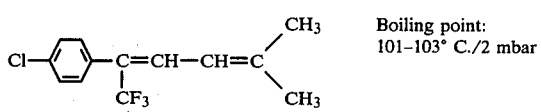 Boiling point: 101-103° C./2 mbar

EXAMPLE 2

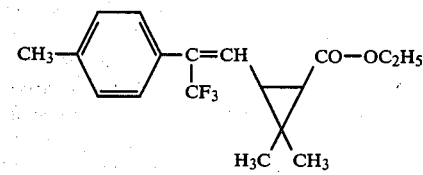

A mixture of 32 g (0.133 mol) of 1,1,1-trifluoro-2-(4-methyl-phenyl)-5-methyl-2,4-hexadiene, 1.2 g of copper powder and 1.5 g of copper sulphate (anhydrous) was heated to 110°-120° C. and a mixture of 16 g (0.067 mol) of 1,1,1-trifluoro-(4-methyl-phenyl)-5-methyl-2,4-hexadiene and 22.8 g (0.2 mol) of diazoacetic acid ethyl ester was then very slowly added dropwise in the course of 4 hours, also at 110°-120° C., while stirring. When the evolution of nitrogen had ended, the mixture was cooled, diluted with 300 ml of methylene chloride and then filtered. The filtrate was extracted by shaking with 500 ml of water, the organic phase was subsequently separated off and dried over magnesium sulphate and the solvent was then distilled off under a waterpump vacuum. The oily residue was distilled in vacuo. Two fractions were thereby obtained:

Fraction 1: Boiling point: 80°-93° C./2 mbar;
Fraction 2: Boiling point: 95°-145° C./2 mbar.

Fraction 1 proved to be unreacted 1,1,1-trifluoro-2-(4-methyl-phenyl)-5-methyl-2,4-hexadiene. Fraction 2 was distilled again. 12.2 g (18.7% of theory) of 2,2-dimethyl-3-(2-trifluoromethyl-2-(4-methyl-phenyl-vinyl)cyclopropanecarboxylic acid ethyl ester were then obtained as a yellow oil with a boiling point of 122°-145° C./2 mbar.

The following compounds were obtained analogously:

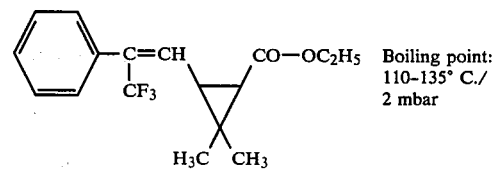 Boiling point: 110-135° C./ 2 mbar

-continued

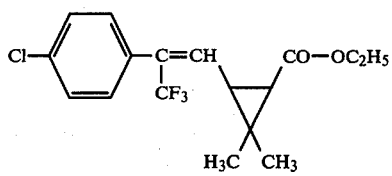

EXAMPLE 3

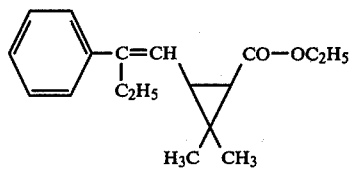

51.2 g (0.2 mol) of 1-phenylpropyl-phosphonic acid diethyl ester, dissolved in 30 ml of anhydrous tetrahydrofuran, were added dropwise to a mixture of 24 g (0.214 mol) of potassium tert.-butylate and 300 ml of anhydrous tetrahydrofuran at 20°–25° C., while stirring. After the mixture had been subsequently stirred at 20°–25° C. for a further 2 hours, 34 g (0.2 mol) of cis/-trans-2,2-dimethyl-3-formyl-cyclopropanecarboxylic acid ethyl ester, dissolved in 50 ml of anhydrous tetrahydrofuran, were added dropwise at 25° C., while stirring. Stirring was then continued at 60° C. for a further 6 hours. 500 ml of water were then added and the reaction mixture was extracted twice with 300 ml of methylene chloride each time. The organic phases were separated off and dried over magnesium sulphate, the solvent was distilled off under a waterpump vacuum and the residue was distilled in vacuo. 28.3 g (52% of theory) of 2,2-dimethyl-3-(2-ethyl-2-phenyl-vinyl)cyclopropanecarboxylic acid ethyl ester (isomer mixture) were obtained as a yellow oil with a boiling point of 142°–150° C./2 mbar.

The following compounds were obtained analogously:

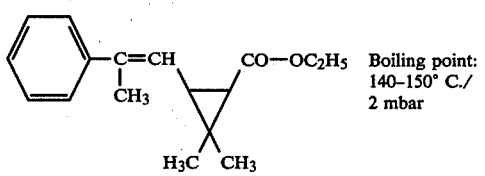 Boiling point: 140–150° C./2 mbar

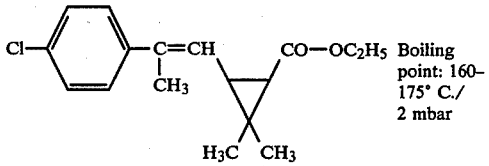 Boiling point: 160–175° C./2 mbar

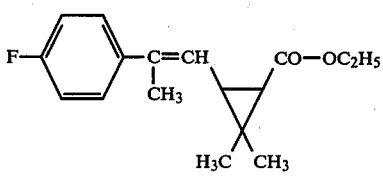

EXAMPLE 4

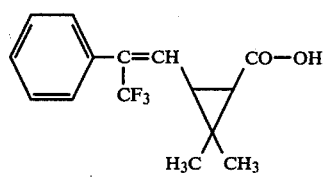

21 g (0.067 mol) of 2,2-dimethyl-3-(2-trifluoromethyl-2-phenyl-vinyl)-cyclopropanecarboxylic acid ethyl ester were dissolved in 100 ml of ethanol, a solution of 3.1 g of sodium hydroxide in 75 ml of water was then added and the mixture was heated to the reflux temperature for 4 hours, while stirring. The ethanol was then distilled off under a waterpump vacuum, the residue was taken up in 300 ml of water and the aqueous mixture was extracted once with 300 ml of methylene chloride. The aqueous phase was separated off, acidified with concentrated hydrochloric acid and then extracted twice with 300 ml of methylene chloride. The organic phases were then separated off, dried over magnesium chloride, and the solvent was distilled off under a waterpump vacuum. Last residues of solvent were removed by brief incipient distillation at a bath temperature of 60° C. under 2 mbar. 7 g (36.8% of theory) of 2,2-dimethyl-3-(2-trifluoromethyl-2-phenyl-vinyl)-cyclopropanecarboxylic acid were then obtained as a very viscous light yellow oil.

The following compounds were obtained analogously:

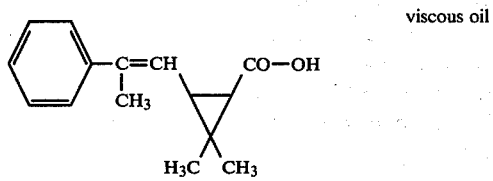 viscous oil

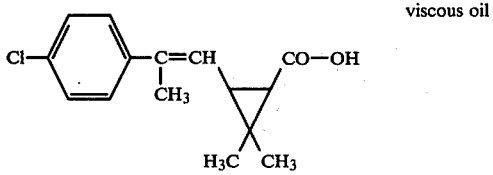 viscous oil

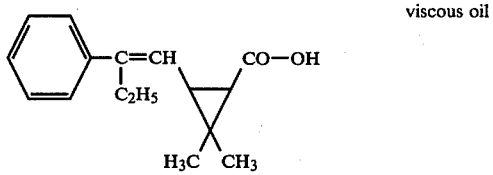 viscous oil

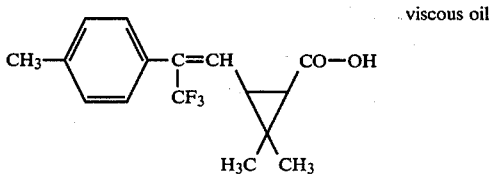 viscous oil

-continued

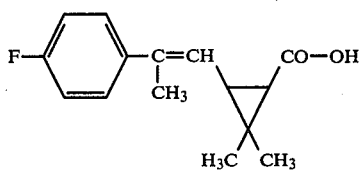

viscous oil

EXAMPLE 5

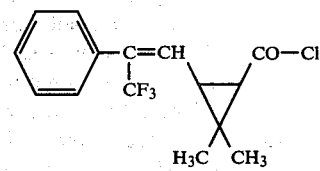

7.1 g (0.025 mol) of 2,2-dimethyl-3-(2-trifluoromethyl-2-phenyl-vinyl)-cyclopropanecarboxylic acid were dissolved in 100 ml of carbon tetrachloride, and 9 g of thionyl chloride were slowly added dropwise at 25° C., while stirring. The mixture was then heated to the reflux temperature for 4 hours. After this reaction time, excess thionyl chloride and carbon tetrachloride were distilled off under a waterpump vacuum. The oil which remained was freed from last residues of solvent by brief incipient distillation at a bath temperature of 40° C./2 mm Hg. 7 g (92.7% of theory) of 2,2-dimethyl-3-(2-trifluoromethyl-2-phenyl-vinyl)-cyclopropanecarboxylic acid chloride were obtained. The structure was confirmed by the $^1$H-NMR spectrum.

$^1$H-NMR spectrum (CDCl$_3$/TMS): aromatic-H: 2.4–2.9τ (m/5H), vinyl-H: 3.28–3.6 and 3.76–4.05τ (m/1H), cyclopropane-H: 7.5–8.33τ (m/2H) and dimethyl-H: 8.5–8.9τ (m/6H).

The following compounds were obtained analogously:

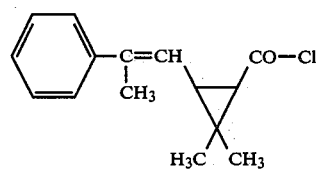

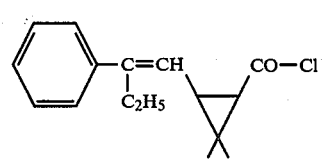

Boiling point: 141–145° C./ 2 mm Hg

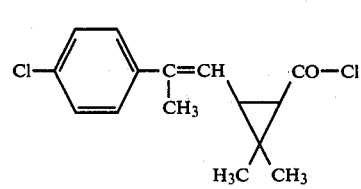

-continued

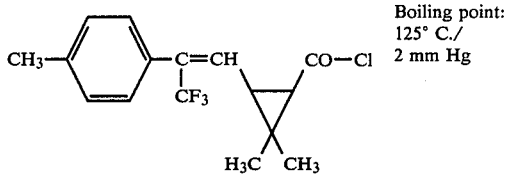

Boiling point: 125° C./ 2 mm Hg

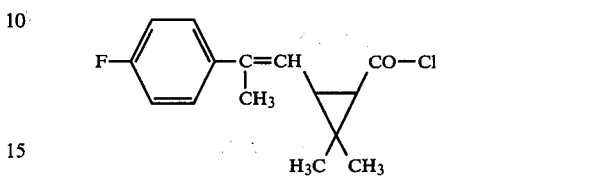

EXAMPLE 6

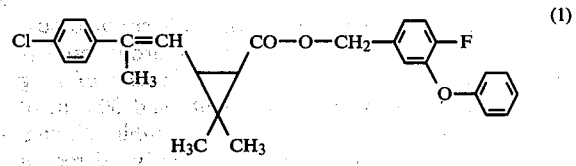 (1)

5.4 g (0.025 mol) of 3-phenoxy-4-fluoro-benzyl alcohol and 7 g (0.025 mol) of 2,2-dimethyl-3-(2-methyl-2-(4-chlorophenyl)-vinyl)-cyclopropanecarboxylic acid chloride were dissolved in 100 ml of anhydrous toluene, and 2.5 g of pyridine, dissolved in 50 ml of anhydrous toluene, were added dropwise at 20°–25° C., while stirring. Stirring was then continued at 25°–35° C. for a further 3 hours. The reaction mixture was poured into 150 ml of water, to which 5 ml of concentrated hydrochloric acid were added, and the organic phase was separated off and washed again with 100 ml of water. The toluene phase was then dried over sodium sulphate and the solvent was distilled off under a water-pump vacuum. Last residues of solvent were removed by brief incipient distillation at a bath temperature of 60° C./1 mm Hg. 8.7 g (74.9% of theory) of 2,2-dimethyl-3-(2-methyl-2-(4-chlorophenyl)-vinyl)-cyclopropane-carboxylic acid 3-phenoxy-4-fluoro-benzyl ester were obtained as a yellow viscous oil with the refractive index n$_D^{23}$: 1.5735.

EXAMPLE 7

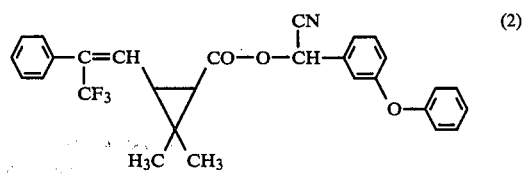 (2)

4.6 g (0.0232 mol) of 3-phenoxy-benzaldehyde and 7 g (0.0232 mol) of 2,2-dimethyl-3-(2-trifluoromethyl-2-phenylvinyl)-cyclopropanecarboxylic acid chloride were together added dropwise to a mixture of 1.8 g of sodium cyanide, 2.7 ml of water, 100 ml of n-hexane and 0.5 g of tetrabutylammonium bromide at 20°–25° C., while stirring, and the mixture was then stirred at 20°–25° C. for 4 hours. 300 ml of toluene were then added and the reaction mixture was extracted by shaking twice with 300 ml of water each time. The organic phase was separated off and dried over magnesium sulphate and the solvent was distilled off under a water-pump vacuum. Last residues of solvent were removed by brief incipient distillation at a bath temperature of 60° C./1 mm Hg. 8.1 g (71.1% of theory) of 2,2-dimethyl-3-(2-trifluoro-methyl-2-phenyl-vinyl)-cyclopropanecarboxylic acid α-cyano-3-phenoxy-benzyl ester were obtained as a viscous oil. The structure was confirmed by the ¹H-NMR spectrum.

¹H-NMR spectrum (CDCl₃/TMS): aromatic-H: 2.3–3.17τ (m/14H), vinyl-H: 3.17–3.5 and 3.78–4.07τ (m/1H), benzyl-H: 3.6–3.75τ (m/1H), cyclopropane-H: 7.67–8.38τ (m/2H) and dimethyl-H: 8.5–9.0τ (m/6H).

The following compounds could be prepared analogously to Example 6 or 7:

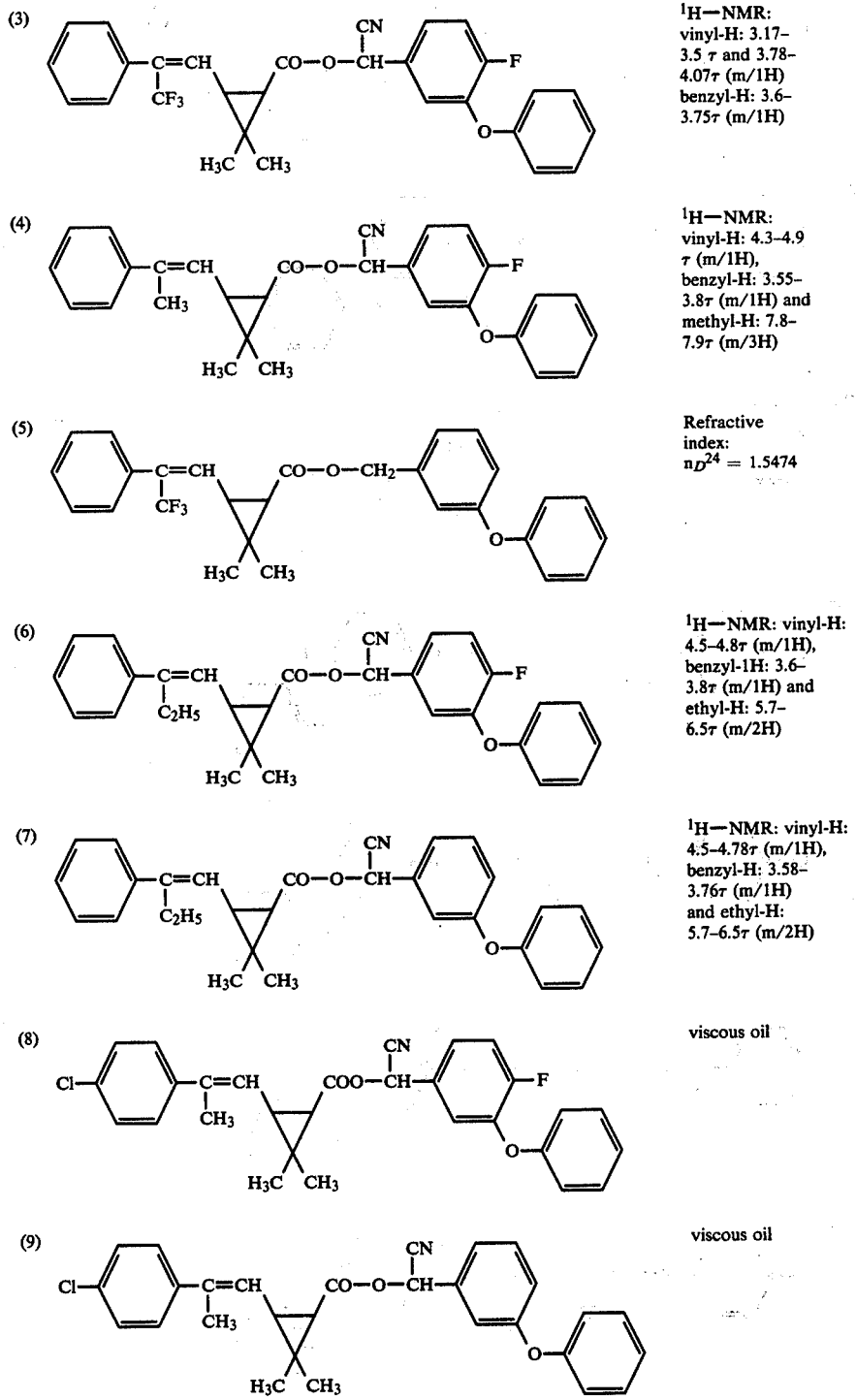

-continued
(10) 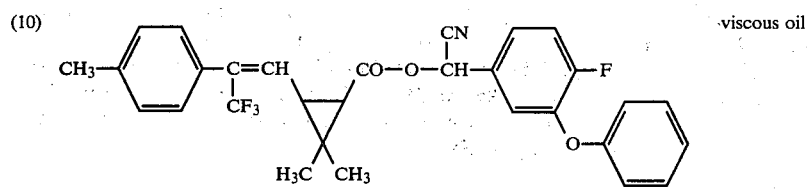 viscous oil
(11) 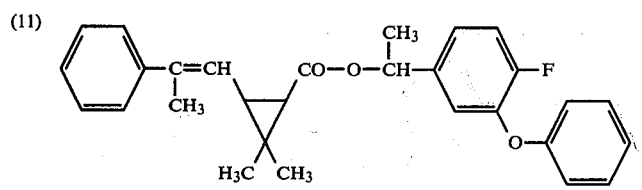
(12) 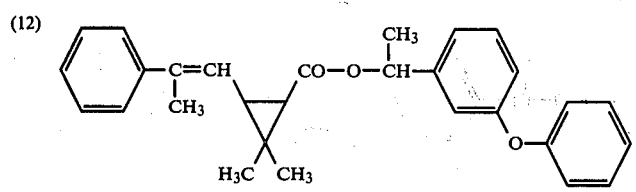
(13) 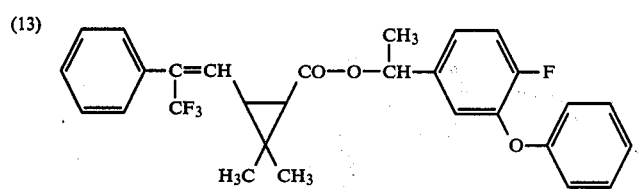
(14) 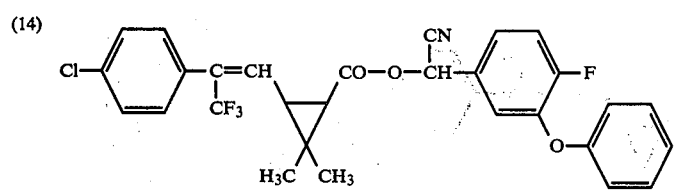
(15) 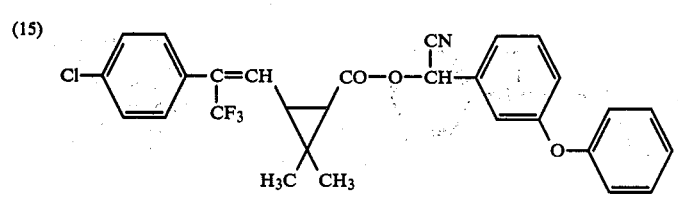
(16) 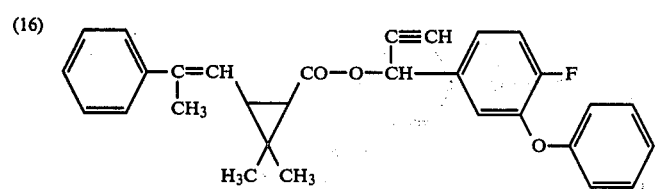
(17) 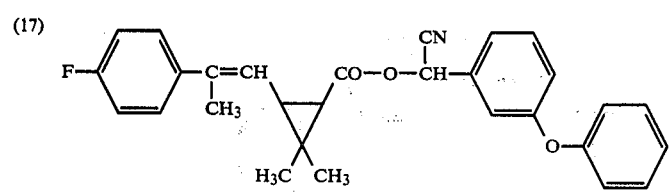

(18) 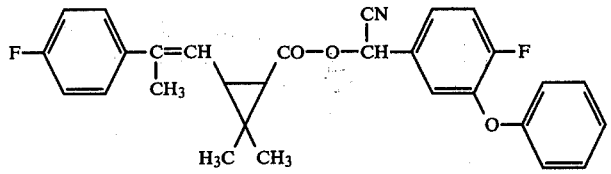

(19) 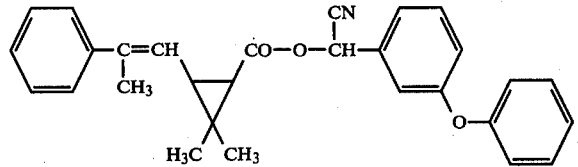

The pesticidal activity of the compounds of this invention is illustrated by the following examples wherein the compounds according to the present invention are each identified by the number (given in brackets) from the preparative examples hereinabove:

EXAMPLE 8

Phaedon larvae test

Solvent: 3 parts by weight of acetone
Emulsifier: 1 part by weight of alkylaryl polyglycol ether To produce a suitable preparation of active compound, 1 part by weight of the active component was mixed with the stated amount of solvent containing the stated amount of emulsifier and the concentrate was diluted with water to the desired concentration.

Cabbage leaves (*Brassica oleracea*) were treated by being dipped into the preparation of the active compound and were infested with mustard beetle larvae (*Phaedon cochleariae*), as long as the leaves were still wet.

After the specified periods of time, the degree of destruction was determined in %: 100% meant that all of the beetle larvae had been killed whereas 0% meant than none of the beetle larvae had been killed.

In this test, for example, the following compounds showed a superior activity compared with the prior art: (9), (8), (3) and (1).

EXAMPLE 9

Myzus test (contact action)

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were treated by being dipped into the preparation of active compound of the desired concentration.

After the specified periods of time, the degree of destruction was determined as a percentage: 100% meant that all of the aphids were killed whereas 0% meant that none of the aphids were killed.

In this test, for example, the following compounds showed a superior activity compared with the prior art: (4), (6), (2) and (3).

EXAMPLE 10

Tetranychus test (resistant)

Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were treated by being dipped into the preparation of the active compound.

After the specified periods of time, the degree of destruction was determined as a percentage: 100% meant that all of the spider mites were killed whereas 0% meant that none of the spider mites were killed.

In this test, for example, the following compounds showed a superior activity compared with the prior art: (4), (9), (8), (6), (2), (3), (1) and (5).

EXAMPLE 11

Test insect: *Phorbia antiqua* grubs in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted hereinafter in ppm (=mg/l). The treated soil was filled into pots and the pots were left to stand at room temperature.

After 24 hours the test insects were introduced into the treated soil and after a further 2 to 7 days the degree of effectiveness of the active compound was determined in % by counting the dead and the live test insects. The degree of effectiveness was 100% if all of the test insects had been killed and was 0% if exactly as many test insects were still alive as in the case of the untreated control.

In this test, for example, the following compounds showed a superior activity compared with the prior art: (1), (4), (8) and (9).

EXAMPLE 12

Test insect: *Agrotis segetum* larvae in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted hereinafter in ppm (=mg/l). The treated soil was filled into pots and the pots were left to stand at room temperature.

After 24 hours the test insects were introduced into the treated soil and after a further 2 to 7 days the degree of effectiveness of the active compound was determined in % by counting the dead and the live test insects. The degree of effectiveness was 100% if all of the test insects had been killed and was 0% if exactly as many test insects were still alive as in the case of the untreated control.

In this test, for example, the following compounds showed a superior activity compared with the prior art: (3), (4) and (8).

EXAMPLE 13

Test with *Lucilia cuprina* res. larvae

Emulsifier:
   35 parts by weight of ethylene glycol monomethyl ether
   35 parts by weight of nonylphenol polyglycol ether To produce a suitable preparation of active compound, three parts by weight of active compound were mixed with seven parts by weight of the above-mentioned solvent mixture and the concentrate thus obtained was diluted with water to the particular desired concentration.

About 20 *Lucilia cuprina* res. larvae were introduced into a test tube which contained approx. 1 cm³ of horse muscle and 0.5 ml of the preparation of active compound. After 24 hours, the degree of destruction was determined.

In this test, for example, the following compounds showed a superior action compared to the prior art: (3), (4), (6), (7), (8), (9) and (1).

EXAMPLE 14

Test with *Boophilus microplus* resistant

Solvent:
   35 parts by weight of ethylene glycol monomethyl ether
   35 parts by weight of nonylphenol polyglycol ether To produce a suitable preparation of active compound, three parts by weight of active compound were mixed with seven parts by weight of the solvent mixture indicated above, and the concentrate thus obtained was diluted with water to the desired concentration.

10 adult *Boophilus microplus* res. were immersed for 1 minute in the active compound preparation to be tested. After transfer to plastic beakers and storage in a climatically controlled chamber, the degree of destruction was determined.

In this test, for example, the following compounds showed a superior action compared with the prior art: (1) to (9).

It will be appreciated that the instant specification and examples are set forth by way of illustration and not limitation, and that various modifications and changes may be made without departing from the spirit and scope of the present invention.

We claim:

1. A 2-phenyl-alk-1-enyl-cyclopropane-carboxylic acid or derivative of the formula

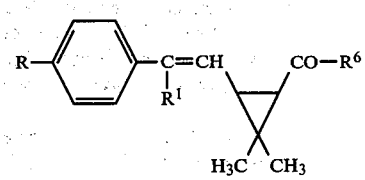

in which
   R is hydrogen or halogen,
   $R^1$ is trifluoromethyl or alkyl of 1-2 carbon atoms, and
   $R^6$ is halogen, OH or $OC_1$-$C_4$-alkyl.

2. A compound according to claim 1, wherein $R^6$ is $-O-C_1$-$C_4$-alkyl.

* * * * *